United States Patent [19]
Berthe

[11] Patent Number: 5,545,773
[45] Date of Patent: Aug. 13, 1996

[54] LIQUID PHASE FLUORINATION PROCESS AND FLUORINATED ORGANIC PRODUCTS RESULTING THEREFROM

[75] Inventor: Bernard Berthe, Marseilles, France

[73] Assignee: Elf Atochem S.A., Puteaux, France

[21] Appl. No.: 279,617

[22] Filed: Jul. 25, 1994

Related U.S. Application Data

[63] Continuation of Ser. No. 988,525, Dec. 10, 1992, abandoned.

[30] Foreign Application Priority Data

Dec. 17, 1991 [FR] France ................................. 91 15630

[51] Int. Cl.⁶ .............................. C07C 17/08; C07C 19/08
[52] U.S. Cl. ........................... 570/167; 570/165; 570/166; 570/168; 570/169
[58] Field of Search ..................................... 570/167, 177, 570/165, 166, 168, 169

[56] References Cited

U.S. PATENT DOCUMENTS 2,005,709  6/1935  Daudt et al. .
5,008,474  4/1991  Wairevens ............................ 570/167

FOREIGN PATENT DOCUMENTS 2388785  11/1978  France .
2652573  4/1991  France .
1585938  3/1981  United Kingdom .

Primary Examiner—Alan Siegel
Attorney, Agent, or Firm—Spencer & Frank

[57] ABSTRACT

In an improved process and plant for carrying out liquid phase fluorination in the presence of a catalyst, consisting in reacting hydrofluoric acid and an organic starting material in a reaction zone, and in separating, in a separating zone, reactional mixture and at least one light fraction containing the desired fluorinated organic products and at least a first part of the sub-fluorinated organic products formed, and a heavy fraction that includes the remainder of the sub-fluorinated organic products formed, and further comprising partial condensation of the said light fraction in order to obtain a gaseous phase containing the desired fluorinated organic products and a liquid phase containing said first part of the said sub-fluorinated organic products, said heavy fraction being returned to said reaction zone and said liquid phase being returned as a reflux to the top of the separation zone, intermediate recovery is carried out at, or in the proximity of, the lower portion of said separation zone.

6 Claims, 1 Drawing Sheet

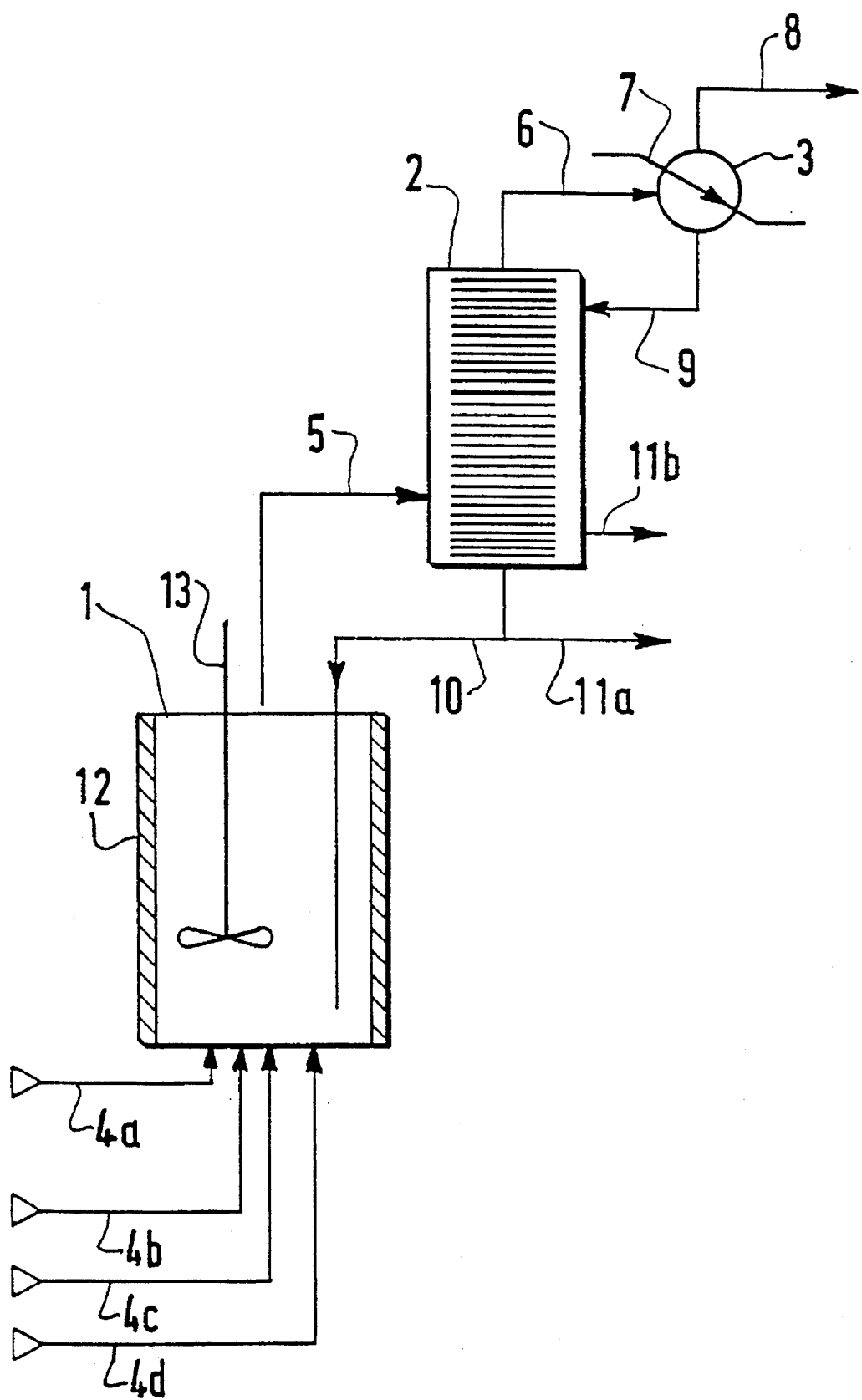

LIQUID PHASE FLUORINATION PROCESS AND FLUORINATED ORGANIC PRODUCTS RESULTING THEREFROM

This is a continuation of application Ser. No. 07/988,525, filed on Dec. 10, 1992, now abandoned.

FIELD OF THE INVENTION

The present invention relates to an improved process for carrying out liquid phase fluorination in the presence of a catalyst. It also relates to fluorine-containing organic products resulting from the use of this process.

BACKGROUND OF THE INVENTION

Processes for carrying out liquid phase fluorination, in the presence of a catalyst, based on the reaction of hydrofluoric acid and a chlorine-containing organic starting material have been known for many years. They are generally implemented in a plant comprising a reactor, a separation column and a condensor. The chlorine-containing organic starting material and the hydrofluoric acid are supplied continuously to the reactor and the products resulting from the reaction, in other words the fluorinated or chloro-fluorinated organic products and the hydrochloric acid formed are recovered from the plant downstream of the condensor.

By way of examples of chloro-fluorinated organic products to which the invention particularly relates, the following can be mentioned without this list constituting in any way a limitation of the invention:

$CFCl_3$ . . . fluorotrichloromethane (F11)

$CF_2Cl_2$ . . . difluorodichloromethane (F12)

$CHClF_2$ . . . chlorodifluoromethane (F22)

$CFCl_2$—$CF_2Cl$ . . . 1,1,2-trichloro-1,2,2-trifluoroethane (F113)

$CF_2Cl$—$CH_2Cl$ . . . 1,2-dichloro-1,1-difluoroethane (F132b)

$CF_3$—$CH_2Cl$ . . . 1-chloro-2,2,2-trifluoroethane (F133a)

$CF_2Cl$—$CH_3$ . . . 1-chloro-1,1-difluoroethane (F142b)

$CFCl_2$—$CH_3$ . . . 1,1-dichloro-1-fluoroethane (F141b)

Obviously, the starting materials, the molar ratios of the reagents, the catalyst, the amount of catalyst as well as the temperature and pressure employed for the reaction, and other things as well, will be chosen as a function of the fluorination products that it is desired to obtain. The catalysts employed are, in this type of reaction, generally those comprising halides of groups IVa, IVb, Va, Vb, VIa, VIb and VIII of the Periodic Table.

Particular use for this purpose is made of pentavalent antimony halides, more particularly antimony pentachloride. Their activity is maintained by permanently adding halogen, particularly chlorine. The halogen and the catalyst form the catalytic system.

It should nevertheless be noted that these fluorination reactions are generally accompanied by parasitic reactions such as dehydrochloration, dimerization trimerization etc. followed by fluorination and/or chlorination. Moreover, by-products generated by impurities which may be present in the organic starting materials can also be formed. These by-products, whether they are the result of parasitic reactions or reactions with impurities that are present, are in certain cases heavier, from-the point of view of their vapor pressure, than the fluorination products that it is desired to obtain.

By virtue of the design of the apparatus, and without any particular steps being taken, a part at least of the by-products formed accumulates in the reactor and leads either to a loss of selectivity by acting on liquid-vapor equilibria, or to deactivation of the catalyst.

Faced with this production of by-products and the need to have full control of the composition of the reaction medium, two techniques have been employed to date:

The first of these consists in employing somewhat drastic fluorination conditions so as to eliminate as much as is possible these by-products by fluorinating them and then "purging" or "sweeping" them by the flow of the principal products at the head of the separation column. This is notably the case in the well known processes for producing the F11, F12, F22 and F113 derivatives which are generally carried out in a concentrated catalytic medium.

The second technique consists in eliminating these by-products by means of purging carried out on the reactor. This is notably the case in processes that are carried out in a diluted catalytic medium of which two examples can be cited: production of F142b (cf. French patent 2 652 573) and the production of F133a described by way of example in this present application (comparative example No. 1).

For various reasons, notably selectivity, the first technique consisting in exercising as much control as possible on the composition of the reaction medium by employing conditions highly oriented towards fluorination, cannot always be applied.

Moreover, the second technique involving the checking of the composition of the reaction medium by removal of reactor content suffers from the disadvantage of creating a heavy flow of catalyst that requires treatment in order to eliminate or recycle it.

SUMMARY OF THE INVENTION

The present invention sets out to overcome the disadvantages of the known processes by monitoring the composition of the reaction medium during liquid phase fluorination carried out in the presence of a catalyst. The process according to the invention actually makes it possible to check with great accuracy the composition of the reaction mass, notably as regards the amounts of catalyst present, and thus to obtain a consistent quality of the fluorinated product prepared. Moreover, the process achieves a significant reduction in possible losses of catalyst or the cost of processing the by-products formed in order to recover therefrom catalyst removed along with said by-products.

The present invention hence provides an improved process for carrying out liquid phase fluorination in the presence of a catalyst, consisting in reacting hydrofluoric acid and an organic starting material in a reaction zone, and in separating, in a separation zone, the reactional mixture into on the one hand at least one light fraction containing the desired fluorinated organic products and at least a first part of the sub-fluorinated organic products formed, and on he other hand a heavy fraction comprising, among other things, the remainder of the sub-fluorinated organic products formed, and consisting further in partial condensation of the said light fraction in order to obtain a gaseous phase containing the desired fluorinated organic products and a liquid phase containing said first part of the said sub-fluorinated organic products, said heavy fraction being returned to said reaction zone and said liquid phase being returned as a reflux to the top of said separation zone, wherein said heavy fraction recovered at the base of said separation zone and comprising, among other things, the remainder of the sub-fluorinated organic product formed furthermore contains a part of the entrained catalyst, and wherein intermediate recovery is carried out at the bottom of said separation zone, or at a level in the proximity thereof corresponding at least to that of a theoretical plate situated above a withdrawal point at the bottom of said column and at least to that of a theoretical plate situated below the reaction mixture feed level of said separation zone.

This new technique has the advantage of considerably reducing the flow of catalyst needing treatment. The catalysts employed, generally antimony chlorofluorides are effectively heavier than the fluorinated organic products that it is sought to obtain, and the above-cited intermediate recovery hence leads to a liquid effluent which has a considerably lower catalyst composition.

Although it might seem obvious to those skilled in the art that the use of intermediate recovery would lead to the removal of less catalyst than if one were to carry out the same at the bottom of the reactor, persons skilled in the art were dissuaded from using this technique as it would seem to them that this involved the disadvantage, when compared with the technique using recovery at the bottom of the reactor, of inherently leading to a build-up of heavy by-products in the bottom of the reactor which would have a harmful effect on the running of the process. However, surprisingly and completely unexpectedly, this does not happen and the process opens up the way for pursuing the running of the process over extremely extended periods with excellent yields.

According to one embodiment, intermediate recovery is carried out on the heavy fraction leaving said separation zone.

According to another embodiment, intermediate recovery is carried out in the lower region of the separation zone on a heavy fraction slightly different from the heavy fraction removed at the bottom of the separation zone and originating from a theoretical stage higher than a stage corresponding to removal carried out at the bottom of said column and below the reaction mixture feed level of the separation zone.

Obviously, the heavy fraction collected at the bottom of the separation zone can equally well be a liquid as well as a gaseous phase. In one embodiment of the invention, provided byway of example below, this preferably consists of a liquid phase.

The choice of operating conditions: temperature of the reactor, pressure, amount of catalyst, starting material feed rate, are adapted suitably in order to obtain the desired fluorination products at the downstream end of the condensor.

The rate of intermediate recovery is adapted so as to keep the heavy matter content of the reaction mass constant at the desired value. Analytical monitoring, for example by chromatography, enables the evolution of the reaction composition to be followed and the flow rate of lateral recovery to be adjusted.

The present invention also provides a liquid phase fluorination installation comprising:

a fluorination reactor supplied with hydrofluoric acid, an organic charge, and a catalyst system;

a line from the head of said reactor and feeding a separation column;

a condensor linked to the head of said column and supplying a gaseous fraction which is recovered, and a liquid fraction which is returned to the head of said column in order to provide reflux thereof;

a collection line located at the bottom of said separation column collecting the heavy fraction at the bottom of said separation column for recycling thereof to the bottom portion of said reactor;

and a recovery line located on said collection line or at an intermediate level comprised between that of a theoretical plate above the level of the bottom of said column and that of a theoretical plate below the feed level of said separation column.

In one embodiment, the recovery line is located at the bottom of the separation column.

In another embodiment the recovery line is located at a level comprised between that of a theoretical plate above the bottom of the separation column and that of a theoretical plate below the feed level of the separation column.

Advantageously, the collection line providing for recycling of the heavy fraction collected at the bottom of the separation column to said fluorination reactor comprises a dipleg.

Further objects and advantages of the present invention will become more clear from the description that follows of an installation suitable for carrying out the process according to the invention, provided by way of non-limiting example.

BRIEF DESCRIPTION OF THE DRAWING

The attached FIGURE applies to the fluorination of trichlorethylene to F133a by catalysis using antimony, but it is obvious that the examples are only given by way of illustration and many other products can be fluorinated without departing from the scope of the invention.

DETAILED DESCRIPTION OF PREFERRED EMBODIMENT

The installation in the FIGURE comprises a stainless steel reactor 1, a separation column 2, a partial, quasitotal or total condensor 3 with gas and liquid outlet.

The lines for introducing the reagents are shown diagrammatically by lines 4a, 4b, 4c, and 4d and these respectively correspond to the trichlorethylene (in other words the organic charge), the hydrofluoric acid, the chlorine, and the antimony pentachloride. These lines may moreover be grouped together into a single conduit line. Line 5 links the head of reactor 1 to separation column 2, line 6 links the head of separation column 2 to a condensor 3, which is cooled by a refrigerant fluid line 7 and of which a line 8 at the head thereof enables the desired fluorinated organic product to be recovered along with volatile substances including chlorine and hydrofluoric acid that have not reacted; line 9 links the bottom of condensor 3 to the head of separation column 2 and ensures reflux in the latter. A collection line 10 links the bottom of separation column 2 to the bottom part of reactor 1 to ensure recycling; line 10 is preferably materialized by a dipleg. Recovery is achieved using either a line 11a provided on line 10, or a side stream line 11b disposed at an intermediate level on separation column 2, comprised between a theoretical plate above the level of the bottom portion and a theoretical plate below the feed by line 5.

Reactor 1 is provided with a double jacket 12 enabling the temperature inside it to be regulated, and with an agitating or stirring device 13.

Line 8 enables a gaseous fraction to be recovered containing the fluorinated organic product resulting from the process and residual volatile products, including the chlorine and hydrofluoric acid which have not reacted; line 11a or 11b enable a flow of the heavy fraction containing part of the entrained catalyst that has collected at the bottom portion of separation column 2, or at an intermediate level, to be recovered.

The fractions withdrawn by line 8 are passed on to treatment stages for recovering products and optionally recycling them. The rate of addition of antimony pentachloride is adjusted so as to preserve a constant antimony content in the reaction medium inside the reactor. Recovery of the heavy fraction by line 11a or 11b is regulated so as to keep the level of heavy products in the reaction medium constant.

The flow rate on line 9 is adjusted so as to obtain a reflux flow which is such that only a mixture containing chlorine and hydrofluoric acid that have not reacted together with by-product hydrochloric acid and the desired fluorinated organic product, in this case product F133a, is collected in the gaseous phase by line 8. The liquid phase separated by condensor 3 containing sub-fluorinated products, notably F132b, is recycled to separation column 2.

EXAMPLES

Examples are provided below which were obtained in a pre-production laboratory installation comprising a reactor having a capacity of 20 liters, in 316L stainless steel, a separation column, a condensor and a phase separator of the type conventionally used in the laboratory.

Example 1 corresponds to running of a process using the state of the art, consisting in direct recovery at the bottom portion of the reactor whereas examples 2 and 3 correspond to operating the process in accordance with the invention using intermediate recovery carried out on the heavy phase, in the present case the liquid phase, in the lower region of the separation column.

EXAMPLE 1—Direct Recovery at the Bottom of the Reactor

The operating conditions of the installation were as follows:

reactor temperature . . . 130° C.

operating pressure . . . 17 bar abs reactor antimony content . . . 1% by weight

F133a productivity: 1.5 mole/h/liter of reactor chlorine throughput: 2.5 molar on the basis of the trichloroethylene The hydrofluoric flow rate was regulated in order to keep the reaction volume constant. Reflux was adjusted to produce a zero F132b content in the distillate.

The rate at which liquid was directly drawn off from the reactor was adjusted so as to maintain the percentage of heavy products in the reactor at 60% by weight.

The rate of recovery at the bottom portion of the reactor necessary to maintain this content was 0.22 kg/h. The purged matter contained 1% by weight of antimony. Thus, 2.2 g/h antimony was drawn off which it was necessary to compensate by feeding the reactor with 5.4 g/h $SbCl_5$ in order to maintain a constant catalyst content inside the reactor.

EXAMPLE 2—Intermediate Recovery on the Heavy Fraction at the Bottom Portion of the Separating Column The percentage of heavy matter in the reactor was maintained at the same value as above in other words 60% by weight, but intermediate recovery was now implemented on the liquid phase leaving at the bottom of the separation column, using line 11a.

The reaction and reflux conditions were identical to those in example 1. The rate of recovery needed to maintain the above content was 0.40 kg/h. The intermediate product drawn off did not contain in excess of 100 ppm antimony. Hence, 0.04 g/h of antimony was recovered.

Running was continued under these conditions for 800 hours. The reactor composition was monitored by chromatography. After 800 hours, the chromatogram was identical to the one obtained after 100 hours operation. No new product appeared and there was no accumulation of the heaviest products. Recovery at the bottom portion of the separating column hence enables the reactor composition to be maintained.

These two comparative examples clearly demonstrate the value of intermediate recovery at the bottom portion of the separating column when compared to direct recovery at the bottom of the reactor, as far as the extracted catalyst contents are concerned. The antimony content of the fraction extracted by recovery carried out in accordance with example 2 (hence at the bottom portion of the separation column) was 100 times lower than the antimony content of the fraction withdrawn from the reactor when operation proceeded as in comparative example 1. After 100 hours, the equivalent of the whole catalytic charge in the reactor had been removed by direct recovery on the reactor. As against this, more than 6000 hours operations are necessary to remove the equivalent amount when using intermediate recovery at the bottom portion of the separating column, as in example 2.

EXAMPLE 3—Recovery at the Bottom of the Separating Column (Different Reflux Conditions to Example 2)

The same operating conditions were used as in example 2 but the reflux flow rate was however adjusted in the separating column, at the condensor stage, in order to obtain a 1% F132b content based on the amount of F133a recovered downstream of the condensor.

The rate at which intermediate recovery needed to be accomplished on line 11a at the bottom of the column in order to maintain the heavy matter content in the reactor at 60% by weight, was 0.28 kg/h. The antimony content of the recovered matter was 100 ppm.

The rate of intermediate recovery needed to maintain the heavy matter content in example 2 in the reactor was about 80% higher than that which would be achieved by taking liquid off directly at the bottom of the reactor (example 1). If the rate of reflux is reduced (example 3), then the rate of side stream recovery diminishes and is about 25% higher than that in example 1.

Considered from the aspect of ease of plant operation and the treatment of recovered matter, the enormous advantage of intermediate recovery when compared to direct recovery at the bottom of the reactor becomes obvious.

EXAMPLE 4—Intermediate Recovery on a Heavy Fraction of the Separation Column at a Height Thereof Slightly Above That for Heavy Fraction Recovery The same conditions as described in example 2 were used, but employing intermediate recovery at a height in the separation column corresponding to that of a theoretical plate above that corresponding to the very bottom of the separation column. In this case, the recovery line, instead of being connected to line 10, was located on the lower portion of separation column 2 at a higher level than the point at which removal via line 10 takes place. This line is identified by reference numeral 11b. Obviously, although recovery in this example took place at a level corresponding to the height of a theoretical stage situated at a higher level than the bottom of the column, recovery can also be done at an even higher level.

Results that were substantially identical to those obtained in the case of example 2 were obtained and the same conclusions apply.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

What is claimed is:

1. A process for carrying out liquid phase fluorination in the presence of a catalyst, comprising the steps of:

(a) reacting hydrofluoric acid and an organic starting material in a reaction zone to obtain a reaction mixture;

(b) flowing the reaction mixture to a separation zone having top, median and bottom levels, the reaction mixture being introduced at the median level;

(c) separating this reaction mixture into a light fraction and a heavy fraction, wherein the light fraction obtained from the top level comprises the desired fluorinated organic products and a portion of the sub-fluorinated organic products, and wherein the heavy fraction comprises the remainder of the sub-fluorinated products and the catalyst;

(d) partially condensing said light fraction to obtain a gaseous phase and a liquid phase, wherein the gaseous phase contains the desired fluorinated organic products and the liquid phase being returned as a reflux to the top of the separation zone;

(e) regulating recovery of a portion of said heavy fraction provided in step (c) to maintain the level of heavy products in said reaction zone substantially constant; and (f) recycling the remainder of said heavy fraction provided in step (c) to the reaction zone.

2. The process of claim 1, wherein step (e) is carried out at the bottom of the separation zone.

3. The process of claim 1, wherein step (e) is carried out at a level comprised between the bottom of the separation zone and below introduction of the reaction mixture at the median level of the separation zone.

4. The process of claim 1 wherein said catalyst is selected from an antimony chloro-fluoride class of catalysts.

5. The process of claim 1 wherein said catalyst is antimony pentachloride.

6. A process for carrying out liquid phase fluorination in the presence of a catalyst, based on a reaction of hydrofluoric acid and a chlorine-containing organic starting material to make a chloro-fluorinated organic product selected from the group consisting of fluorotrichloromethane (F11), difluorodichloromethane (F12), chlorodifluoromethane (F22), 1,1,2-trichloro-1,2,2-trifluoroethane (F113), 1,2-dichloro-1,1-difluoroethane (F132b), 1-chloro-2,2,2-trifluoroethane (F133a), 1-chloro-1,1-difluoroethane (F142b) and 1,1-dichloro-1-fluoroethane (F141b); said process comprising the steps of:

(a) reacting the hydrofluoric acid and the chlorine-containing organic starting material in the presence of the catalyst in a reaction zone to obtain a reaction mixture;

(b) flowing the reaction mixture to a separation zone having top, median and bottom levels, the reaction mixture being introduced at the median level;

(c) separating the reaction mixture in the separation zone into a light fraction and a heavy fraction, wherein the light fraction obtained from the top level comprises the desired fluorinated organic product and a portion of the sub-fluorinated organic products, and wherein the heavy fraction comprises the remainder of the sub-fluorinated products and the catalyst;

(d) partially condensing said light fraction to obtain a gaseous phase and a liquid phase, wherein the gaseous phase contains the desired fluorinated organic product and the liquid phase is returned as a reflux to the top of the separation zone;

(e) regulating recovery of a portion of said heavy fraction provided in step (c) to maintain the level of heavy products in said reaction zone substantially constant; and (f) recycling the remainder of said heavy fraction provided in step (c) to the reaction zone.

* * * * *